United States Patent
Krueger

(10) Patent No.: US 9,121,835 B2
(45) Date of Patent: Sep. 1, 2015

(54) QUALITY INSPECTION OF CONTAINER COATINGS

(71) Applicant: KRONES AG, Neutraubling (DE)

(72) Inventor: Jochen Krueger, Hagelstadt (DE)

(73) Assignee: KRONES AG, Neutraubling (DE)

( * ) Notice: Subject to any disclaimer, the term of this patent is extended or adjusted under 35 U.S.C. 154(b) by 343 days.

(21) Appl. No.: 13/728,343

(22) Filed: Dec. 27, 2012

(65) Prior Publication Data

US 2013/0186331 A1    Jul. 25, 2013

(30) Foreign Application Priority Data

Jan. 24, 2012   (DE) .................... 10 2012 200 976

(51) Int. Cl.
| | | |
|---|---|---|
| *G01N 33/00* | (2006.01) | |
| *C23C 16/52* | (2006.01) | |
| *C23C 16/04* | (2006.01) | |

(52) U.S. Cl.
CPC .......... *G01N 33/0004* (2013.01); *C23C 16/045* (2013.01); *C23C 16/52* (2013.01); *B29C 2945/76143* (2013.01)

(58) Field of Classification Search
CPC .......... B29C 2945/76143; B29C 2945/76381; B29C 45/1701; B29C 45/76; B29K 2067/00; G01N 2030/8886; G01N 30/88
See application file for complete search history.

(56) References Cited

U.S. PATENT DOCUMENTS

| | | | |
|---|---|---|---|
| 5,898,058 A * | 4/1999 | Nichols et al. ................ | 528/286 |
| 6,228,447 B1 * | 5/2001 | Suzuki et al. ................ | 428/35.7 |
| 6,500,506 B1 * | 12/2002 | Suzuki et al. ................ | 428/35.7 |
| 6,531,193 B2 | 3/2003 | Fonash et al. | |
| 7,041,350 B1 * | 5/2006 | Rule et al. ................ | 428/35.7 |
| 2002/0094402 A1 * | 7/2002 | Jen ................ | 428/36.92 |
| 2002/0136808 A1 * | 9/2002 | Rule ................ | 426/131 |
| 2002/0198331 A1 * | 12/2002 | Nishihara et al. ........... | 525/444 |
| 2006/0169026 A1 | 8/2006 | Kage et al. | |
| 2006/0287472 A1 * | 12/2006 | Jernigan ................ | 528/272 |
| 2008/0292781 A1 | 11/2008 | Rius et al. | |
| 2010/0034985 A1 * | 2/2010 | Krueger et al. ............. | 427/579 |

(Continued)

FOREIGN PATENT DOCUMENTS

| | | |
|---|---|---|
| DE | 4042557 | 11/1996 |
| DE | 19738721 | 3/1999 |
| DE | 10242086 | 4/2004 |

(Continued)

OTHER PUBLICATIONS

Notification of the First Office Action, The State Intellectual Property Office of the People's Republic of China, Application No. 201310016210.5, dated Sep. 24, 2014.

(Continued)

*Primary Examiner* — David A Rogers

(74) *Attorney, Agent, or Firm* — Marshall, Gerstein & Borun LLP

(57) ABSTRACT

A method and apparatus are disclosed for testing and inspecting containers coated by means of a plasma treatment, e.g. plastic bottles, which are coated for instance with amorphous silicon oxide or carbon compounds. The containers are tested by a measuring device trace-gas-analytically, e.g. mass-spectrometrically, for undesired foreign substances, such as acetaldehyde and/or antimony, escaping from the container material after a plasma coating treatment.

19 Claims, 1 Drawing Sheet

(56) References Cited

U.S. PATENT DOCUMENTS

2011/0093214 A1    4/2011    Nagano et al.
2011/0154883 A1*   6/2011    Squicciarini et al. ........ 73/23.35

FOREIGN PATENT DOCUMENTS

| DE | 102004042431 | 3/2006 |
| DE | 102010012501 | 9/2011 |
| EP | 0 306 307 | 3/1989 |
| EP | 1273677 | 1/2003 |

OTHER PUBLICATIONS

Search Report in DE Application No. 10 2012 200 976.0 dated Mar. 20, 2012.

Kim et al., "Real Time Spectroscopic Ellipsometry: In Situ Characterization of Pyrrole Electropolymerization", Journal of the Electrochemical Society, vol. 138, Issue 11, pp. 3266-3275 (1991).

\* cited by examiner

QUALITY INSPECTION OF CONTAINER COATINGS

FIELD OF THE INVENTION

The invention relates to a method and an apparatus for the quality inspection of coatings of containers, in particular the inspection of plastic bottle coatings obtained by a plasma treatment.

BACKGROUND

The plasma deposition of gas barrier layers in plastic bottles includes the deposition of layers, for instance, of amorphous silicon oxide (SiOx) or carbon compounds (e.g. diamond-like carbon "DLC"), with the aim to prevent the permeation of gases, such as CO2 or oxygen, through the plastic material. Additionally, with respect to the inside coating of bottles, e.g. plastic bottles made of polyethylene terephthalate (PET), the migration of foreign substances from the plastic into the product can be prevented. Examples for such foreign substances in connection with PET are, above all, acetaldehyde or antimony. However, also bottle materials based on other synthetic materials contain, for instance, plasticizers which partially only have a weak bond to the substrate material.

In particular after a thermal treatment of the bottles, such as a plasma treatment, the release of undesired substances from the bottles is clearly encouraged. Experience has shown that PET bottles having an inadequate layer quality already have an unpleasant strong smell of acetaldehyde after one thermal treatment or plasma coating process.

In addition, it is the purpose of a plasma coating to prevent the absorption of sterilization media like PAA or H2O2 into the bottle material as this may result in a delayed release of undesired foreign substances into the product contained in the bottle.

The thicknesses of these plasma layers, which will also be referred to as barrier layers below, are within a range of ten to some hundred nanometers and are invisible, in particular in the case of silicon oxide.

The following methods are known for monitoring the coating quality:

Classical measuring devices, e.g. from companies like PreSens or Mocon (Ox-tran), may be used for the detection of permeation substances, e.g. gases, penetrating the bottle wall.

The coating may also be tested with modern layer analyzing methods, e.g. Fourier transform infrared spectroscopy (FTIR) techniques as described in U.S. Pat. No. 6,531,193 or EP 1 273 677, or by ellipsometry (see, for instance, J. Electrochem. Soc., Volume 138, Issue 11, pp. 3266-3275, 1991).

Another method is a so-called acid test in which the bottles are exposed to an aggressive medium, such as concentrated sulfuric acid. Uncoated bottles are attacked by the medium and become dull, while coated bottles show a certain protection against the medium.

All of these methods have the disadvantage that they take a very long time (some minutes to some days), or that the bottle has to be destroyed for analyzing it.

Furthermore, it is known, for instance from US020080292781A and DE102010012501, that a faster inspection of the plasma coating can be accomplished by means of light spectroscopy test methods, where the intensity of specific spectral lines of the plasma contained in the bottle is compared with a predefined reference intensity and, if the spectral line intensities are sufficiently congruent, it will be assumed that the plasma coating has worked. However, this method measures the plasma coating only indirectly, and an accurate, complete plasma coating representing an intact gas barrier cannot be determined with certainty.

Therefore, it is an object of the disclosure to provide an apparatus and a method to improve the inspection of coated containers, for instance of plastic bottles, coated by a plasma treatment.

SUMMARY

According to some aspects of the disclosure, this is achieved by a method according to claim 1 and an apparatus according to claim 8. Advantageous embodiments and further developments are defined in the dependent claims.

In some aspects, the disclosure takes advantage of the fact that if containers, e.g. plastic bottles, are provided with a barrier layer obtained by a plasma coating, the escape of undesired foreign substances from the container material is nearly entirely suppressed. Consequently, containers that have a complete and intact barrier layer have a neutral smell. In a method according to some aspects, a container coated by a plasma treatment can be tested for undesired foreign substances, such as acetaldehyde and/or antimony, escaping from the container material by means of a trace gas analytical test, e.g. by a mass spectrometer.

In some aspects, a trace gas analytical test has the advantage that an inspection of the quality or intactness of the container coating obtained by a plasma treatment can be carried out within a short time, e.g. less than 0.1, 1, 10, 100 ms per container, by determining the presence or absence of undesired foreign substances escaping from the container material.

In some aspects, the aforementioned short test periods are enough to allow the direct testing of the containers ("inline") for escaping undesired foreign substances, that is, at the speed at which they run through the production process and treatment process. This has the advantage that the containers need not be measured on a sample basis in a complicated and time-consuming manner once the containers are coated, and that each individual container can be measured.

In some aspects, it is possible that a coating treatment, for instance by means of a plasma treatment, and/or another thermal treatment of the container is directly followed by a trace gas analytical test of the air contained in the container for undesired foreign substances escaping from the container material without the necessity to rinse the container with a standard gas, e.g. technically purified air, before. To this end, for instance, a sampler may be used, which can be introduced into the container or may be disposed directly above the container opening (within a distance of 0.1, 1, 5 or 10 cm, preferably 1 to 2 cm, from the container opening) and which passes a part of the air contained in the container on to a measuring device, e.g. a trace gas analyzer, in order to allow the testing thereof for the presence and concentration of, or the absence of undesired foreign substances escaping from the container material.

In some aspects, advantageously it is also possible, however, to blow/rinse a standard gas, such as ambient air, technically purified air, an inert gas, a noble gas, a noble gas mixture or a combination of the aforementioned gases into the container to be inspected and to have the mixture of standard gas and possible substances escaping again from the container material, also referred to as test gas, tested by a measuring device for undesired foreign substances escaping from the container material.

In some aspects, the quality of the barrier layer produced by means of a plasma treatment can be quantified, for instance, in that a limit value for the concentration of an undesired foreign substance can be predefined and, for instance, if the limit value for the concentration is exceeded by more than 0.1, 1, 5, 10 or 100%, the tested container can be classified and/or marked, for instance, as inadequately coated and/or is finally removed from the production and/or transferred to a new plasma coating treatment. Predefining the limit values for the concentration of an undesired foreign substance may additionally be dependent on the temperature of the container to be tested, for instance the internal temperature of the container. It is conceivable, for instance, that a higher limit value for the concentration of an undesired foreign substance can be tolerated if the temperature rises, e.g. at temperatures of 30° C., 50° C. or more of the container to be tested, as compared, for instance, to containers which have internal temperatures that correspond to room temperatures. By such a feasible determination of the limit value for the concentration of an undesired foreign substance in dependence on the internal temperature of the container it is possible to take the internal temperature fluctuations of the containers to be tested into account in the test for undesired foreign substances. Internal temperature fluctuations of the containers to be tested may occur, for instance, as a result of fluctuations in the ambient conditions, e.g. summer/winter, day/night, draft, etc.

In another advantageous embodiment, it is possible that the container to be tested is inoculated with one or more tracer substances, e.g. a food contact uncritical substance such as xenon, prior to the plasma coating treatment and that the container is then, after the plasma coating treatment, tested in a trace gas analysis for tracer substances escaping from the container material. To this end, it is possible, for instance, to add a tracer to the blow air of a stretch blow molding machine in order to inoculate the container during the shaping thereof.

BRIEF DESCRIPTION OF THE DRAWINGS

The figures show by way of example.

DETAILED DESCRIPTION

Figure 1:
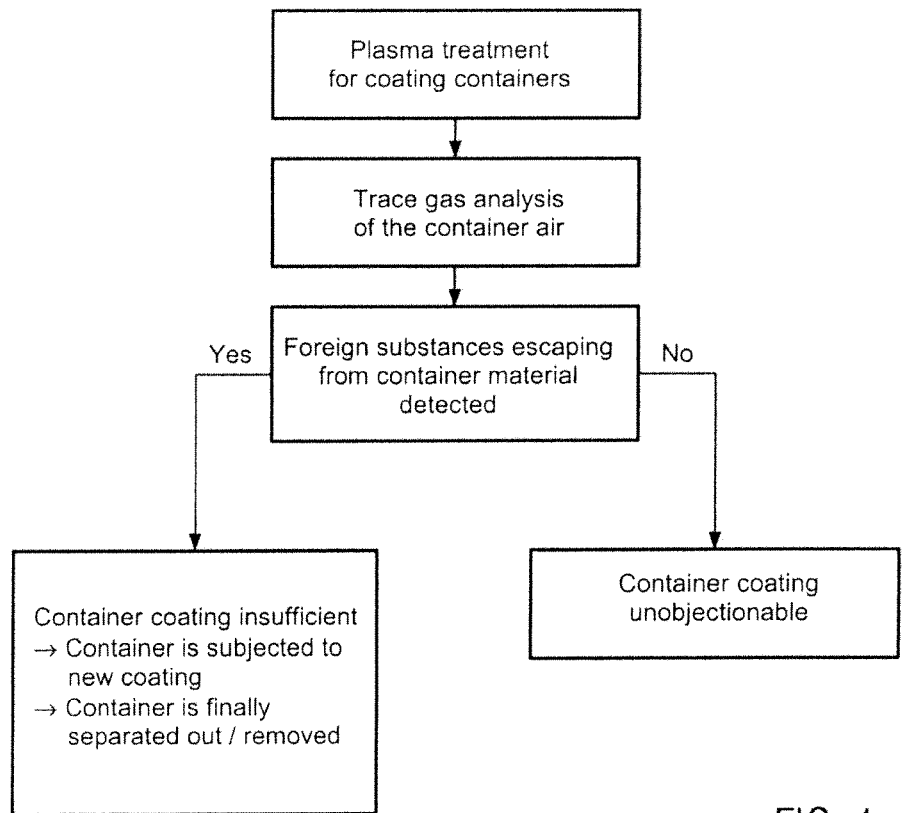
FIG. 1: an exemplary process diagram.

FIG. 1 describes by way of an example an advantageous method implementation.

First, a container may be coated, for instance, by a plasma treatment. Then, the coating can be tested by means of a trace gas analysis, for instance, by testing the container air or container test gas for undesired foreign substances escaping from the container material or tracers escaping from the container material. If no undesired foreign substances and/or tracers escaping from the container material or concentrations of said substances lower than predefined limit values are detected, then the coating may be classified, for instance, as unobjectionable.

However, if undesired foreign substances and/or tracers escaping from the container material or concentrations of said substances higher than predefined limit values are measured, then the container coating can be classified, for instance, as inadequate and/or insufficient and the objected container can either be transferred to a new coating treatment or be finally taken out of the production process and removed.

Figure 2:
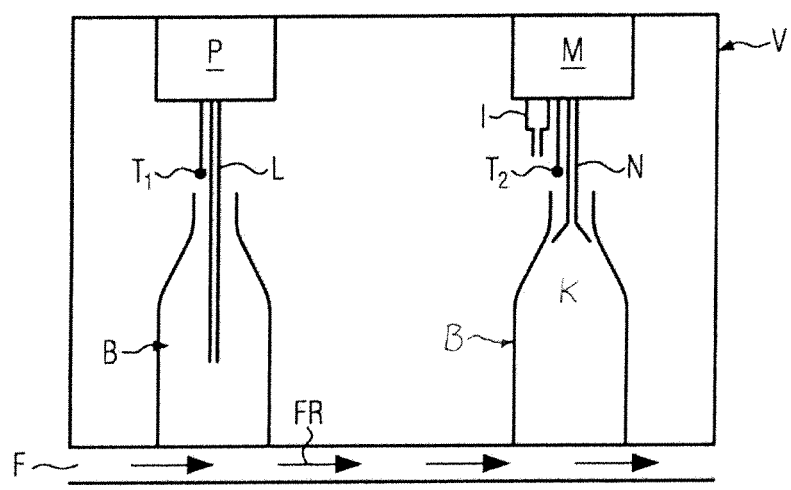
FIG. 2: an exemplary apparatus arrangement.

FIG. 2 schematically shows an example for an advantageous embodiment of an apparatus V for coating containers, for instance by means of a plasma treatment, and for the subsequent testing of coated containers for undesired foreign substances escaping from the container material or tracers escaping from the container material. The apparatus may comprise a unit for coating containers B, for instance a plasma treatment unit P, which can supply gas to the container B, for instance by means of a gas lance L, and ignite plasma for the coating of the container. The apparatus V may include a container conveyor F, which can guide the coated container B to a measuring device M where the container B can be tested for undesired foreign substances or tracers escaping from the container material, for instance in a trace gas analysis. The measuring device M can include, for instance, a sampler N, which can partially pass the air contained in the container B on to the measuring device M.

Furthermore, it is also possible that the measuring device M additionally includes at least one injection unit I and at least one sampler N, and that the at least one injection unit I can blow a standard gas into a container B to be tested and the at least one sampler N can sample at least a part of the test gas K escaping from a container to be tested and pass it on to the measuring device M.

For controlling the temperature of the containers B to be treated and tested, the apparatus V for coating the containers B and subsequently inspecting the coating may include at least one temperature sensor which can measure, for instance, the internal temperature of the container B to be treated and/or tested. FIG. 2 shows by way of example two temperature sensors T1 and T2, which can be introduced into a container B so as to measure, for instance, the internal temperature thereof. Thus, for instance, the plasma treatment unit P may comprise a temperature sensor T1 and/or the measuring device M a temperature sensor T2.

In the figures, the reference numbers designate:
B Container, e.g. a plastic bottle.
V Apparatus for coating containers, e.g. by means of a plasma treatment, and for the subsequent testing of coated containers for undesired foreign substances escaping from the container material or tracers escaping from the coating material.
P Plasma treatment unit for coating containers.
L Gas lance for gas supply and ignition of the plasma.
M Measuring device, e.g. a mass spectrometer, for the trace gas analysis of the container air or test gas, respectively, for undesired foreign substances escaping from the container material or tracers escaping from the coating material.
N Sampler, capable of transferring container air and/or test gas to the measuring device.
F Conveyor unit for containers.
FR Direction of movement of the conveyor unit for containers.
T1, T2 Temperature sensor(s).

What is claimed is:

1. A method for testing and inspecting containers comprising container material coated by means of a plasma treatment the method comprising the step:
    testing the containers trace-gas-analytically by a measuring device for undesired foreign substances escaping from the container material after a plasma coating treatment,
    wherein the containers are tested inline for undesired foreign substances at the speed at which the containers run through a production process and treatment process.

2. A method according to claim 1, wherein air contained in the container is tested for undesired foreign substances escaping from the container material by means of a sampler.

3. A method according to claim 1, wherein a test gas comprising a standard gas including at least one of ambient air, technically purified air, an inert gas, a noble gas, a noble gas mixture, and a combination of the aforementioned gases, is blown into a container to be tested, and wherein at least a part of the test gas escaping from the container is tested by a measuring device for one or more undesired foreign substances escaping from the container material.

4. A method according to claim 1, wherein the containers comprise plastic bottles, and wherein the plastic bottles are coated with at least one of amorphous silicon oxide and carbon compounds.

5. A method according to claim 1, wherein the containers are tested mass spectrometrically.

6. A method according to claim 1, wherein the foreign substances comprise at least one of acetaldehyde and antimony.

7. A method according to claim 1, wherein the containers are tested within a test period of less than 100 ms per container.

8. A method according to claim 7, wherein the containers are tested within a test period of less than at least one of 0.1, 1 or 10 ms per container.

9. A method according to claim 1, further comprising the steps:
  inoculating the container to be tested with one or more tracer substances prior to the plasma coating treatment; and
  testing the container after the plasma coating treatment in a trace gas analysis for tracer substances escaping from the container material.

10. A method according to claim 9, wherein the one or more tracer substances include at least one of a food contact uncritical substance.

11. A method according to claim 10, wherein the one or more tracer substances comprise xenon.

12. A method for testing and inspecting containers comprising container material coated by means of a plasma treatment, the method comprising:
  testing the containers trace-gas-analytically by a measuring device for undesired foreign substances escaping from the container material after a plasma coating treatment,
  wherein when it is detected that a predefined limit value in concentration of a specific undesired foreign substance is exceeded by more than at least one of 0.1, 1, 5, 10 or 100%, then the container is at least one of a) classified as inadequately coated, b) finally removed from production, and c) transferred to a new plasma coating treatment.

13. A method according to claim 12, wherein the predefined limit value in the concentration of the specific undesired foreign substance depends on the temperature of the container to be tested, wherein the predefined limit values in the concentration for a container having an internal temperature of 30° C., 50° C., or more are higher than the predefined limit values for a container having an internal temperature that corresponds to room temperature.

14. An apparatus for coating containers with a coating by means of a plasma treatment and for the testing and inspection of the coating, the containers formed of a container material, the apparatus comprising:
  at least one plasma treatment unit for coating the containers; and
  at least one measuring device comprising a mass spectrometer, wherein the measuring device is configured to be capable of testing the containers coated by the plasma treatment unit for undesired foreign substances escaping from the container material.

15. An apparatus according to claim 14, wherein the measuring device additionally comprises at least one sampler, configured such that the at least one sampler can sample at least a part of air contained in the container to be tested and pass the air on to the measuring device.

16. An apparatus according to claim 14, wherein the measuring device additionally comprises at least one injection unit and at least one sampler, configured such that the at least one injection unit can blow a test gas comprising standard gas into a container to be tested and the at least one sampler can obtain a sample of at least a part of the test gas escaping from the container to be tested and pass the sample on to the measuring device.

17. An apparatus according to claim 14, wherein the measuring device additionally comprises at least one temperature sensor which is arranged to measure the temperature of a container to be at least one of treated and tested.

18. A method for testing and inspecting a container made of plastic and coated with a barrier layer by means of a plasma treatment, the method comprising the steps:
  obtaining a sample of gases from inside the container after the plasma treatment while the container is being transferred along a production line;
  testing the sample with a trace gas analyzer to identify a concentration of an undesirable foreign substance in the sample;
  comparing the concentration to a predefined limit value;
  classifying the container as either unobjectionable or objectionable depending on whether the concentration is above or below the predefined limit value; and
  inoculating the plastic with a tracer substance prior to coating the plastic with the barrier layer, wherein the undesirable foreign substance comprises the tracer substance.

19. The method of claim 18, further comprising the step:
  injecting a test gas into the container prior to obtaining the sample.

* * * * *